(12) United States Patent
Lemonnier

(10) Patent No.: US 7,344,878 B2
(45) Date of Patent: Mar. 18, 2008

(54) STERILE BOX FOR MICRO-ORGANISM CULTURE, SET AND DISPENSER OF BOXES

(75) Inventor: Jean Lemonnier, Paris (FR)

(73) Assignee: Developpement Techniques Plastiques Holding (D.T.P. Holding), Izermore (FR)

( * ) Notice: Subject to any disclaimer, the term of this patent is extended or adjusted under 35 U.S.C. 154(b) by 790 days.

(21) Appl. No.: 10/250,675

(22) PCT Filed: Jan. 10, 2002

(86) PCT No.: PCT/FR02/00083

§ 371 (c)(1),
(2), (4) Date: Nov. 25, 2003

(87) PCT Pub. No.: WO02/057405

PCT Pub. Date: Jul. 25, 2002

(65) Prior Publication Data

US 2004/0072339 A1 Apr. 15, 2004

(30) Foreign Application Priority Data

Jan. 18, 2001 (FR) .................................. 01 00679

(51) Int. Cl.
*C12M 1/22* (2006.01)

(52) U.S. Cl. ............................. 435/305.4; 435/305.1; 435/810

(58) Field of Classification Search ............. 435/305.3, 435/305.4; 220/257.1
See application file for complete search history.

(56) References Cited

U.S. PATENT DOCUMENTS

| | | | | |
|---|---|---|---|---|
| 3,337,416 A | * | 8/1967 | Forgacs | 435/287.4 |
| 3,816,264 A | | 6/1974 | Winter et al. | |
| 4,709,819 A | | 12/1987 | Lattuada et al. | |
| 5,021,351 A | * | 6/1991 | Ervin | 435/305.1 |
| 5,398,837 A | * | 3/1995 | Degrassi | 220/835 |

FOREIGN PATENT DOCUMENTS

| | | |
|---|---|---|
| EP | 447893 | 9/1991 |
| FR | 2436084 | 4/1980 |
| FR | 2486915 | 1/1982 |

* cited by examiner

*Primary Examiner*—Wiliam H. Beisner
(74) *Attorney, Agent, or Firm*—Dennison, Schultz & MacDonald

(57) ABSTRACT

A sterile housing for the cultivation of micro-organisms has a container closed by a cover with a culture medium within the walls and base. The cover has a bottom forming a base and walls connected to the bottom, and the lid is set on the container and includes a peripheral sealing zone having a flat section recessed relative to the bottom of the container. A concave inner seal is fixed to the peripheral sealing zone of the lid to hermetically seal the box by enclosing the container, enabling the inner seal to be removed without exposing the culture medium.

13 Claims, 5 Drawing Sheets

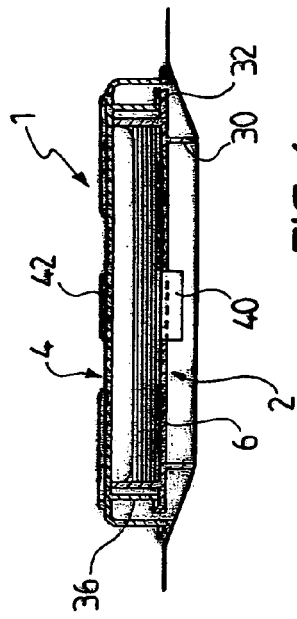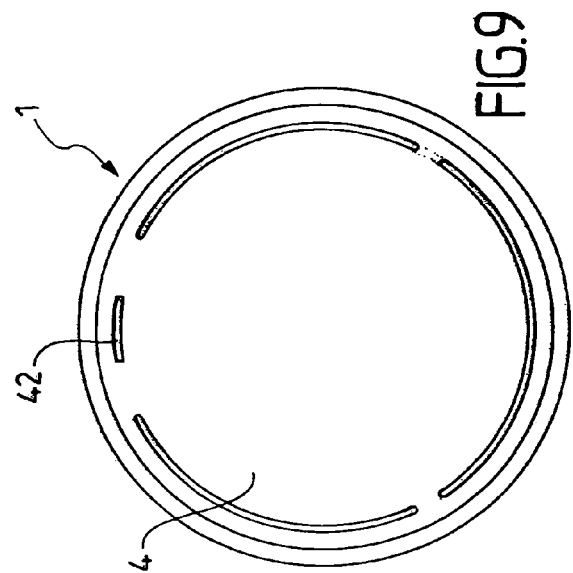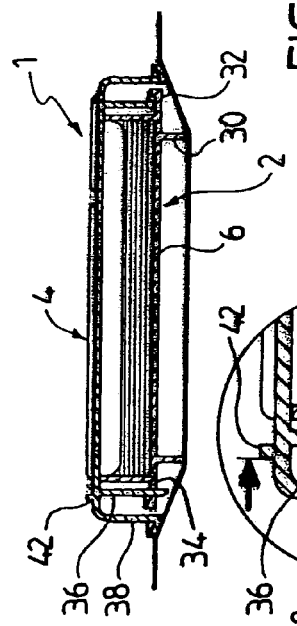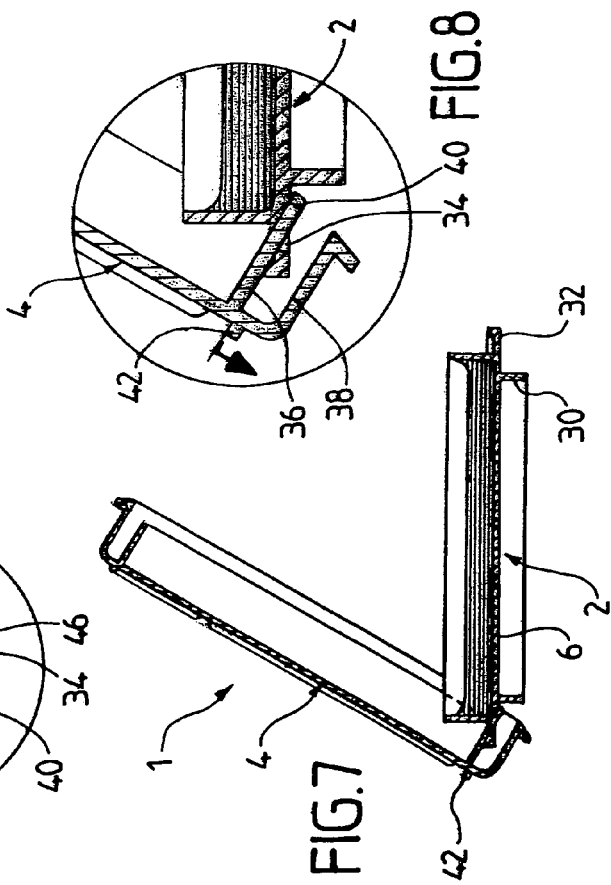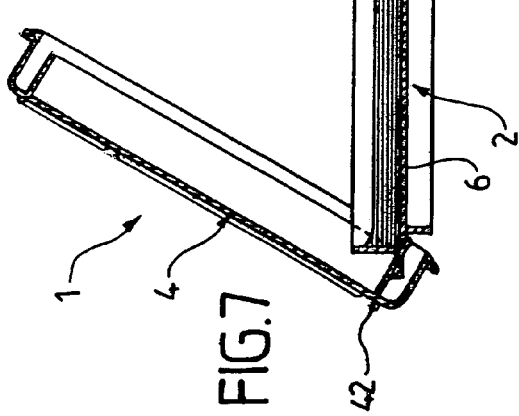

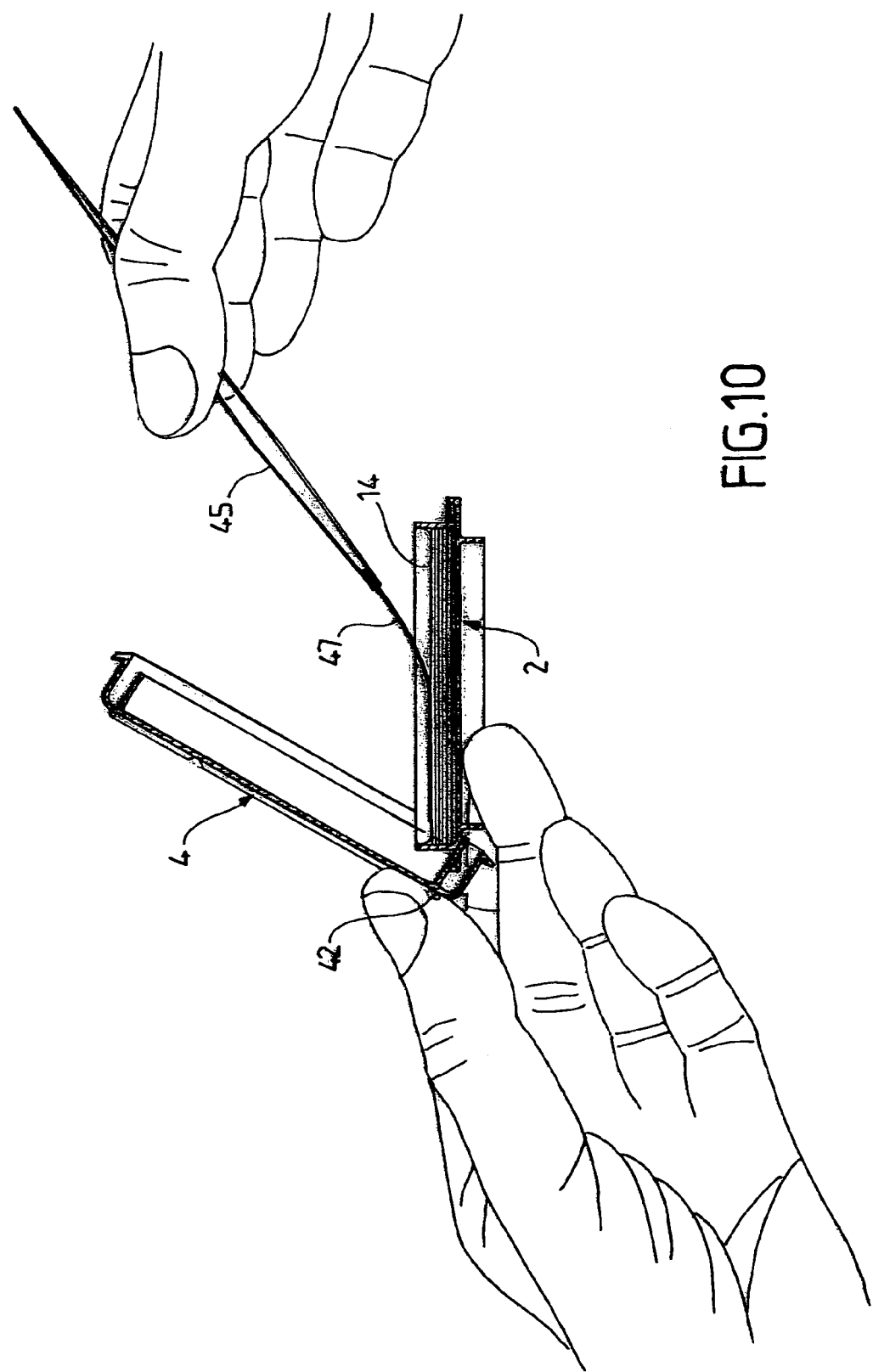

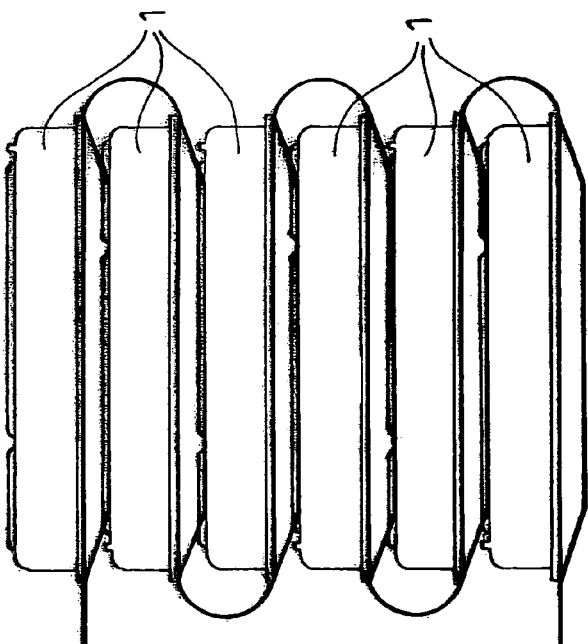

STERILE BOX FOR MICRO-ORGANISM CULTURE, SET AND DISPENSER OF BOXES

Figure 1:
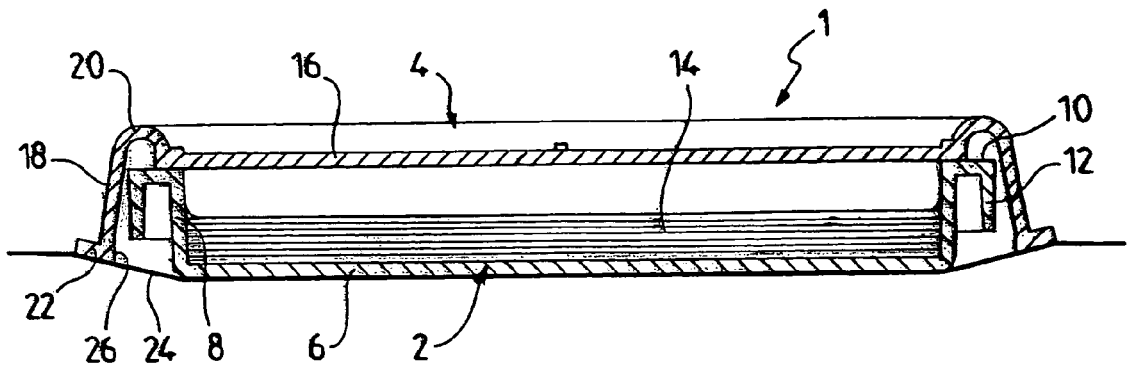

This application is a filing under 35 USC 371 of PCT/FR2002/000083 filed Jan. 10, 2002.

The invention relates to a sterile box for the culture of micro-organisms.

It relates more particularly to a box consisting of a container closed by a lid and capable of containing a culture medium, the container having a bottom and walls joined to the bottom.

Boxes of this type, frequently known as Petri dishes, are generally made from injection-moulded plastics material. They are, preferably, transparent in order to permit visual inspection of the culture medium, e.g. an agar gel medium. These boxes are not sealing-tight. They are packed in a sealing-tight, sterile packaging which contains a plurality of boxes. As soon as the packaging is opened, the sterility of the boxes is no longer guaranteed.

Furthermore, the opening of a pack of boxes, thus exposing them to the ambient air, significantly shortens their expiry date. It is therefore necessary to use the set of boxes from one pack rapidly. Furthermore, in the case of microbiological analysis on a filtering membrane, it is necessary to transfer and deposit on the surface of the culture medium a membrane which may have trapped germs. This operation must be effected under good aseptic conditions. Preferably, this delicate operation is carried out in a control laboratory where the air is clean, or by handling under a laminar flux fume cupboard where the air is filtered and therefore cleared of any possible microbial contamination which might affect the results of the analysis.

With one hand, the operator lifts the lid of the sterile box (Petri dish) which generally rests on a laboratory bench top. With his other hand, he transfers the filtering membrane by means of tweezers from the filtration point to the container of the box in which he deposits the same. He then closes the box and places it upside-down in an incubator.

The removal of the Petri dish from the filtration point of the sample is not favourable and may be the source of exogenous contamination if the air quality is insufficiently good.

The present invention has the very object of proposing a sterile box for the culture of micro-organisms which overcomes these problems. In particular, it proposes ready-to-use boxes which are totally sealing-tight and whose individual expiry date is the same as that of the entire manufacturing batch.

This result is achieved, according to the invention, in that the lid is placed on the container and has a peripheral sealing region formed by a plane face set back from the bottom, forming a seat, of the container in order that the plane face does not touch the surface on which the box is resting, and consequently that a concave protective cover is fixed in a sealing-tight manner to the sealing region of the lid, so as to seal the box hermetically by enveloping the container, and not to expose the culture medium when the protective cover is removed.

By virtue of this feature, each box taken individually is sealing-tight. The boxes may be packed in a package which can be opened without breaking the sealing-tightness of each one. Consequently, it is not necessary to use all the boxes of one package at the same time. Each box retains its own expiry date. It is possible to remove the protective cover in an inappropriate environment, without exposing the culture medium and, accordingly, without instantaneously breaching the sterility of the culture chamber located between the surface of the culture medium and the bottom of the lid.

Preferably, the protective cover is transparent.

The protective cover is formed from a semi-rigid plastics material and its concave shape is advantageously thermoformed.

According to a particular embodiment, the lid of the box has a flexible rim surrounding the walls of the container and capable of being deformed in order to grip the walls of the container.

Preferably, the flexible rim has a projecting part capable of cooperating with a complementary part of the container when the rim is deformed, so as to hold the lid on the container.

By virtue of these features, the grasping and gripping of the outer diameter of the lid between the thumb and index finger of one hand make it possible to keep the container firmly in place in the lid by squeezing the flexible rim of the container and by the engagement of the projecting part of the flexible rim in the complementary part of the container. This arrangement prevents the container from escaping when the box is held the right way up.

In a preferred embodiment, the container has an inverted L-shaped rim which surrounds the walls of the container at least partially, the flexible wall of the lid being capable of gripping the inverted L-shaped rim of the container without causing the walls of the container to deform.

Thus the culture medium, e.g. agar gel, contained in the container is not disturbed by deformation when the box is squeezed between the thumb and index finger.

In a preferred embodiment, the box according to the invention has means of articulating the lid to the container, so as to permit opening and closing within the space of the box with one hand.

In a particular embodiment, articulation means consist of at least one pin provided on the lid and at least one complementary slot provided in the container, into which slot the pin engages.

The possibility also arises of opening or closing the box axially by a vertical movement of the lid. The invention is not restricted to this system of articulating the lid to the container. For example, the lid could be articulated by a hinge or any similar means.

By virtue of the articulation of the lid to the container, the box can be opened and closed instantaneously by one hand. The index finger and/or the middle finger support the bottom of the container. By withdrawing or advancing the thumb slightly which is bearing on the lid, the box is opened or closed instantaneously.

In a particular embodiment, the container has an outer collar and the lid has an inner wall and an outer wall, the pin being provided on the inner wall of the lid and the slot being provided in the collar of the container.

Advantageously the slot in the collar of the container has two stop faces to limit the aperture of the lid. Thus, the angle of aperture of the lid is constant and limited, on the one hand, by the contact of the inner circular wall of the lid, which comes to rest on the inner part of the collar of the container and, on the other hand, by the fact that the pin stops on the outer part, advantageously chamfered, of the slot formed under the bottom of the container. This double stop limits the angle of aperture of the lid to about 60°.

Preferably, the lid is equipped with at least one operating tappet which aids opening of the lid.

Each box may have an individual protective cover. The invention also relates to a set of boxes formed of one strip and of a series of boxes according to the invention, disposed one behind another on the strip, each box being fixed to the strip by its sealing region, the strip acting as a protective cover for each of the boxes.

The boxes can be disposed on one single face of the strip forming the protective cover, or the boxes may be disposed alternately on both faces of the strip. The latter arrangement makes it possible to reduce the gap between two boxes in the case of stacking of the boxes in an identical position (right-side-up or upside-down) when the strip is folded in concertina form.

Finally, the invention relates to a dispenser for boxes according to the invention, these boxes forming part of a set of boxes fixed to a strip forming a protective cover for each box. The dispenser has a storage magazine for the strip; means of driving the strip; means of separating one box from the strip; a plate for receiving the box after it has been separated from the strip.

In order to guide the boxes before their arrival on the separating means, the dispenser advantageously comprises a guide which imparts to the successive boxes of the strip an angle of incline relative to the feed direction of the strip.

When the boxes are disposed opposite one another on the two faces of the strip, the guide pivots between two positions inclined symmetrically relative to the feed direction of the strip, the guide moving from one position to the other according to the face on which the box is fixed.

This dispenser makes possible automatic distribution of the boxes without breaking the strip, which permits the strip to be rolled up and recycled. Thus waste from individual protective covers is avoided.

Figure 2:
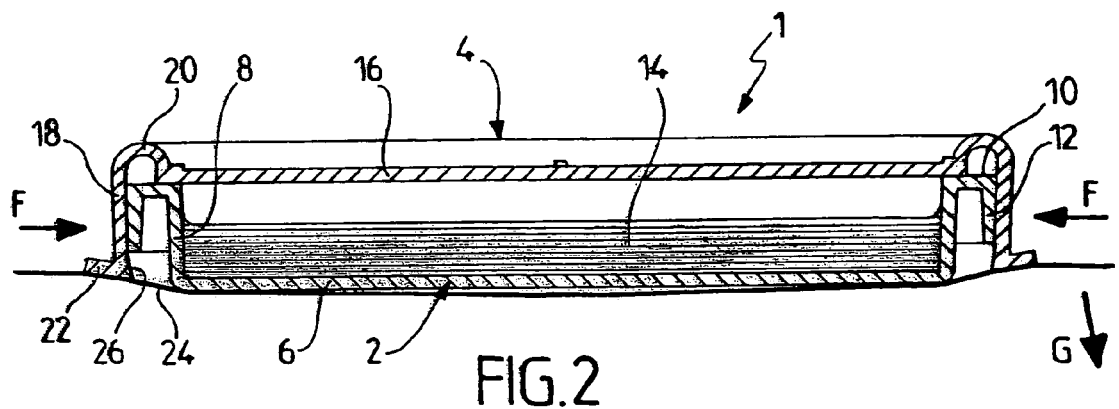
Figure 3:
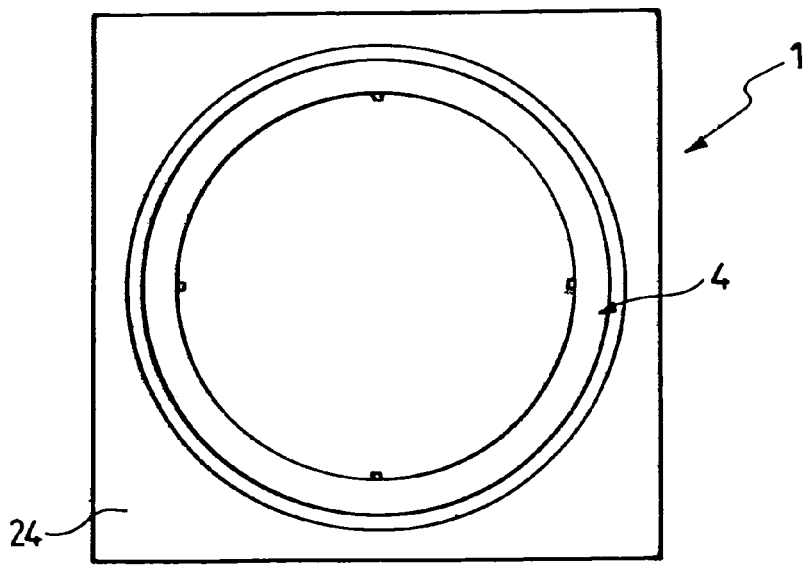
Figure 14:
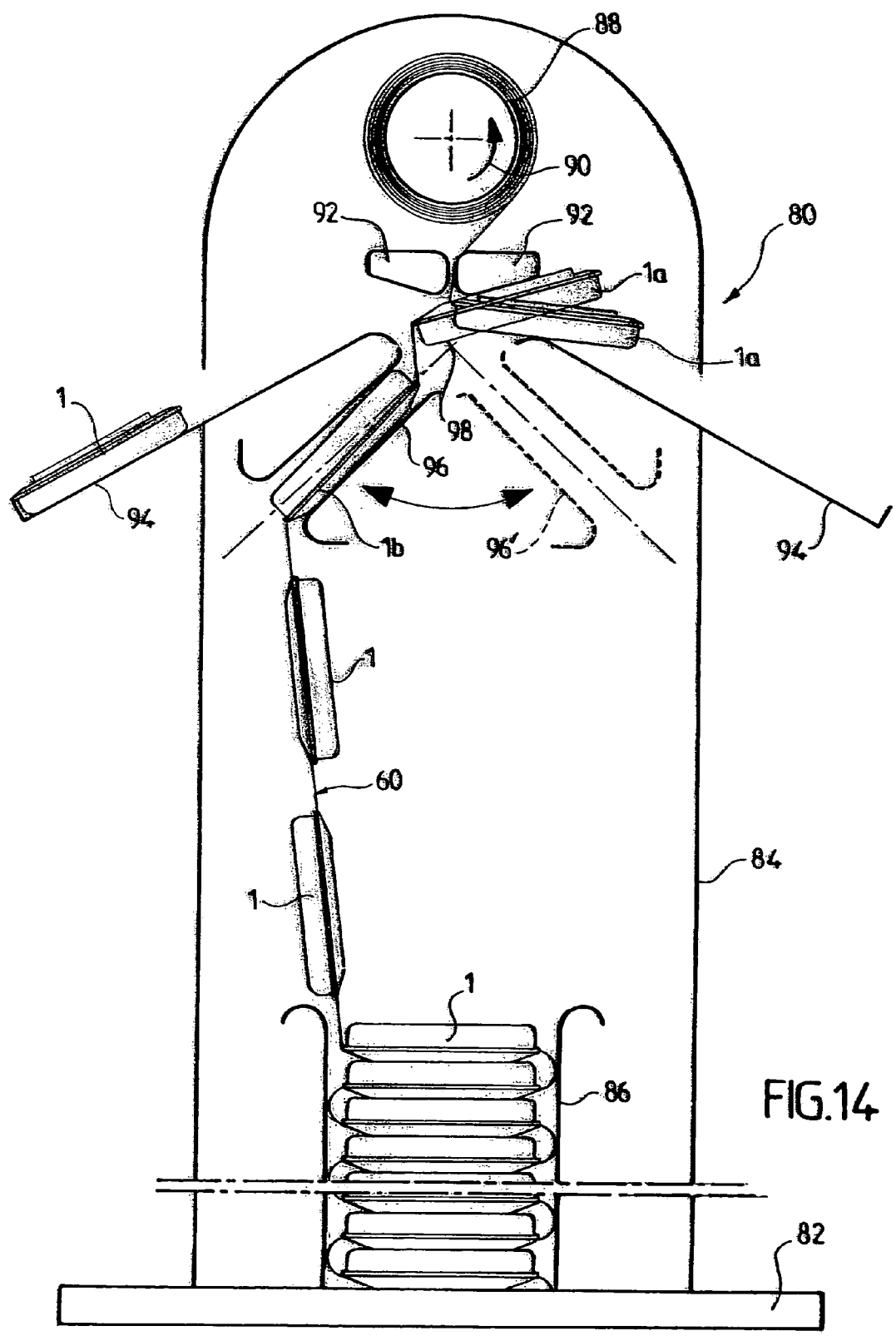

Further features and advantages of the invention will appear from the following description of an embodiment given by way of example with reference to the attached drawings, which show:

FIG. 1, a view in section of a box according to a first embodiment of the invention;

FIG. 2, a view in section of the box shown in FIG. 1 in the position with the lid being squeezed;

FIG. 3, a plan view of the box according to FIGS. 1 and 2;

FIG. 4, a view in section of a box according to a second embodiment of the invention, the lid being in the closed position;

FIG. 5, a detail of FIG. 4, shown to an enlarged scale, whose outer wall of the lid is squeezed on to the outer collar of the container;

FIG. 6, another section view corresponding to that of FIG. 4;

FIG. 7, a view in section of the box shown in FIG. 4 showing the lid in the open position;

FIG. 8 a detail of FIG. 7, shown to an enlarged scale;

FIG. 9, a plan view of the box in FIGS. 4 to 8;

FIG. 10, the position of the fingers of an operator using a box according to FIGS. 4 to 9, the lid being open;

FIG. 11, a set of boxes according to the invention fixed to a single face of a strip forming a protective cover for each box;

FIG. 12, a set of boxes according to the invention fixed alternately to both faces of a strip forming a protective cover for each box;

FIG. 13, the set of boxes according to FIG. 12 after folding of the strip in concertina form in order to form a stack of boxes; and FIG. 14, a dispenser of boxes according to the invention FIGS. 1 and 2 show views in section of a first embodiment of a sterile box 1 according to the invention. The box 1 is formed of a container 2 surmounted by a lid 4. The container 2 has a bottom 6, which forms a seat and to which are connected vertical walls 8. In the example, the bottom 6 is circular and the walls 8 are circular-cylindrical. The walls 8 end with a horizontal flange 10, themselves extended by a collar 12 substantially parallel to the walls 8 The collar 12 forms with the flange 10 and the walls 8 an inverted L-shaped rim.

The container 2 is capable of containing a culture medium 14. This medium is for example an agar gel culture medium set in the container 2.

The lid 4 has a wall 16 of circular shape which closes the container 2 by resting on the horizontal flange 10. The lid 4 has a flexible rim 18 connected to the circumference of the wall 16 by a rounded part 20 intended to promote the flexibility of the rim 18.

The lid 4 further comprises a peripheral sealing region. In the example shown, this region is formed by a plane face 22 located at the end of the flexible rim 18 and surrounding the container 2. As can be deduced from FIG. 1, the plane face 22 is set back from the bottom 6 of the container 2. A semi-rigid protective cover 24 (FIGS. 1 to 3) is fixed to the plane face 22, e.g. heat-sealed, adhered or fixed by any other means to the plane face 22.

The box is closed by the bottom, and the protective cover 24 keeps the entire interior of the box sterile by sealing the container 2 entirely from the bottom 6 thereof. In other words, the container is entirely contained within the inner volume defined by the lid 4 and the protective cover 24. Furthermore, since the plane face 22 is set back from the bottom 6 of the container 2, the protective cover 24, viewed from the outside, has a concave form. A slight prestressing of this protective cover permits the lid 4 to be kept bearing on the flange 10 of the container 2.

The box shown in FIGS. 1 to 3 has individual sterility protection ensured by the semi-rigid protective cover 24. Each box has its own protective cover, in this case square, such that the boxes forming part of one package do not lose their sterility unless the protective cover 24 is removed.

The surface of the culture medium 14 is visible through a single transparent wall, i.e. the wall 16 of the lid 4. The visibility is therefore optimal, which permits inspection of the surface of the agar gel culture medium 14 before the protective cover 24 is peeled off.

In the embodiment described, the box is circular and its diameter is about 70 mm, which makes it possible to hold easily between the thumb and other fingers of the hand. The box may also be oval, polygonal or have another r shape.

The protective cover 24 is formed of a plastics material and is transparent.

As can be deduced from FIG. 2, the flexible rim 18 makes it possible to keep the container 2 firmly in place in the lid 4 by squeezing the outer diameter of the collar 12. In the example shown, the interior of the flexible rim 18 has a projecting part 26 capable of engaging under the rim 12 of the container 2 when the flexible rim 18 is gripped between the thumb and index finger of one hand, as is indicated by the arrows F. In the example shown, the projecting part is formed by an under-cut 26, which ensures that the lid 4 locks over the container 2. The under-cut prevents the container from slipping when the box is held the right way up, the outer wall of the lid being held tight.

Furthermore, the flexible rim 18 bears on the collar 12. This makes it possible to squeeze the lid without causing deformation of the vertical walls 8 and, consequently, without deforming the culture medium 14. In order to remove the protective cover, one end thereof is pulled, as is shown by the arrow G in FIG. 2, then the cover is peeled off.

FIGS. 4 to 10 show a second embodiment of a sterile box for the culture of micro-organisms in order to carry out microbiological analysis. This embodiment is distinguished by the fact that it comprises means of articulating the lid to the container, so as to permit opening and closing of the box with one hand. In the example shown, the bottom 6 of the container 2 is equipped with a circular seat ridge 30, formed for example of three parts set at 120° from one another, on which the container rests when it is placed the right way up, e.g. on a laboratory bench top. The bottom 6 is extended at its edge by a collar 32 which has, preferably, the shape of a hollow dome, so as to aid centring of the lid relative to the container. A slot 34 (see in particular FIGS. 5 and 8), intended to receive a pin forming part of the lid, is provided in the collar 32. A plurality of slots, e.g. three, could also be provided in order to permit placing of the lid in different positions on the container.

The lid 4 comprises an inner circular wall 36 and an outer wall 38, also circular. A pin 40 is provided on the inner wall 36 of the lid 4. The lid 4 is also equipped with an operating tappet 42, on which the thumb of one hand comes to bear in order to permit opening and closing of the lid 4.

The box shown in FIGS. 4 to 9 can be held in the space of one hand, e.g. of the left hand of an operator, as is shown in FIG. 10. It can be opened or closed instantaneously by this same hand. The slot 34 comprises stop faces to limit the displacement of the pin 40 and, consequently, the angle of aperture of the lid 4. In the example shown, a first stop face is formed by a chamfer 46 formed towards the interior of the slot 34, and on the other hand by a circular chamfer 48 (FIG. 5). This double stop limits the angle of aperture of the lid 4 to about 60°.

Due to this feature, the box can be placed close to a point of filtration of a sample to be analysed, by being held in one hand. Thus one can with the other hand grasp and transfer a membrane 47 by means of tweezers 45, then deposit the same on the culture medium 14 contained in the box (FIG. 10). The box is opened rapidly, only when necessary, in order to deposit the membrane. The membrane is only moved a few centimetres in a minimum of time. The lid is opened partly, and only by the angle necessary to allow the membrane to be deposited on the culture medium.

Thus the culture medium remains almost constantly covered by the lid, which prevents it from being exposed too much to the environment. Furthermore, the culture medium is protected from the hands holding the box, as these are located behind the lid, which acts as a screen or shield. The risk of accidental contamination caused by the hand holding the box is therefore eliminated. In the case of handling under a horizontal laminar flux fume cupboard, it should be noted that the box, placed close to the point of filtration, is located in the path of the flux. Thus the placing of the membrane on the culture medium is effected in the best aseptic conditions, where no obstacle stands in the way of the flux. Finally, the very short displacement distance of the membrane during testing makes it possible to avoid as much as possible any dripping from the bottom of the membrane and, thus, to keep a liquid film which promotes its contact with the culture medium 14.

The outer wall 38 forms a flexible rim which can be gripped between the fingers of the hand, e.g. the thumb and the index finger in the direction of the arrows F, so as to squeeze the outer diameter of the collar 32. In a manner identical to that described with reference to FIGS. 1 and 2, the lid 4 is thus locked on the container 2 by gripping of the outer diameter of the wall 38, which prevents the container from slipping when the box is held the right way up.

Microbiological analysis on a filtering membrane by means of a sterile box according to the invention is carried out, therefore, in the following manner. After filtration of the sample to be analysed, with the left hand (in the case of a right-handed person) the box is grasped by its diameter between the thumb and index finger and is squeezed in such a manner that the lid holds the container by gripping, as described above. The filtration funnel is removed from its support and, with the right hand, the protective cover is peeled off, pulling downwards. The box is ready to be used.

It is also possible to peel off the protective cover from the box while the latter is upside down and held by the outer diameter of the lid. In this case, it is not necessary to grip the lid between the thumb and index finger, since the container is bearing into the bottom of the lid and is not at risk of falling. With the left hand, the box is taken by top and bottom between the thumb and index finger, the thumb placed on the tappet on the lid, and the index finger under the box. The box is brought close to the filtration support, the right hand grasps the membrane by means of tweezers, and the thumb of the left hand is moved back slightly so that the box opens. The membrane is deposited on the agar gel with the right hand, and the thumb of the left hand is brought back forward, so that the lid closes instantaneously on the container. The box thus upturned is placed in the incubator and, conventionally, after the necessary time for the growth of any microbe or bacterial colonies, counting and identification are carried out if necessary.

A box according to the invention may have an individual protective cover. It is also possible to place a series of boxes on a common protective cover formed by a strip 60, as is shown in FIG. 11. The boxes 1 are sealed one behind another on the sealing-tight protection strip 60. The boxes may be sealed on the same side of the strip 60, as is shown in FIG. 11. They may also be sealed alternately on either side of the strip, as is shown in FIG. 12. This arrangement permits folding of the strip like a concertina and stacking of the boxes in the same direction, e.g. the right way up, reducing to a minimum the length of the strip 60. Such stacking of the boxes, with the strip folded in the manner of a concertina, is shown in FIG. 13. Such a packaging has the advantage of allowing the boxes 1 to be dispensed by an adapted dispenser, such as shown in FIG. 14.

The dispenser 80 shown in FIG. 14 has a base 82 on which is fixed a vertical housing 84. On the front face of the housing 84 is a storage magazine 86, in which is placed a strip 60 similar to that described with reference to FIGS. 12 and 13. The sterile boxes 1 are disposed one behind another on the strip 60, on either side of this strip.

In the upper part of the housing is a roller 88 for driving the strip, which rotates in the direction indicated by the arrow 90. The strip passes between two separation guides 92. At the moment when a box 1 comes into contact with the separation guides 92, the traction force exerted on the strip separates the protective cover from the box. The box pivots, then slides on to a receiving plate 94.

In order to facilitate separation of the box from the strip, it is preferable if the box is presented on the separation guides at a certain angle of incidence, e.g. 45°. For this reason, the invention comprises a tubular guide in which the boxes pass one after another before reaching the separation guides 92. Furthermore, since in the embodiment shown in FIG. 14, the boxes are placed on either side of the strip, the guide 96 is pivoting. It pivots by an angle substantially equal to 90° about an axis 98. In FIG. 14, the guide 96 has been shown in the position which it adopts to present the box referenced 1a at a suitable angle of incidence relative to the two guides 92. When the next box, referenced 1*b*, is presented opposite the separation guide 92, the pivoting guide will be in the position shown in dotted lines and referenced 96'. Thus the pivoting guide 96 alternatively adopts positions symmetrical to the vertical plane of symmetry of the frame 84 substantially corresponding to the feed direction of the strip 60. After separation, the boxes are received in the symmetrical plates 94 in an inverted position. They are therefore ready to use.

Obviously, the invention is not limited to the embodiments described above by way of example and is capable of numerous modifications.

The invention claimed is:

1. Sterile box for the culture of micro-organisms, comprising:
    a container adapted for containing a culture medium, the container defined by a bottom and walls joined to the bottom,
    a lid resting upon and closing the container, the lid having a peripheral portion extending beyond the walls of the container and comprising a peripheral sealing region formed by a planar face forming a seat set back from the bottom of the container, such that the planar face does not touch a surface on which the box rests, and
    a protective concave cover fixed in a sealing-tight manner to the peripheral sealing region of the lid and externally to the bottom of the container, so as to hermetically seal the box by enveloping the container, and so as not to expose the culture medium in the container when the protective cover is removed.

2. Box according to claim 1, wherein the protective cover is transparent.

3. Box according to claim 1, wherein the lid comprises a flexible rim surrounding the walls of the container, the rim being deformable so as to grip the walls of the container.

4. Box according to claim 3, wherein the flexible rim comprises a projecting part constructed and arranged for cooperating with a complementary part of the container when the rim is deformed, so as to keep the lid on the container.

5. Box according to claim 3, wherein the container comprises an inverted L-shaped rim which at least partially surrounds the walls of the container, the flexible wall of the lid being capable of griping the L-shaped rim of the container without causing deformation of the walls of the container.

6. Box according to claim 3, comprising means for articulating the lid to the container, so as to permit opening and closing within the space of the box with one hand.

7. Box according to claim 6, wherein the means for articulating comprises at least one pin provided on the lid and by at least one complementary slot provided in the container, in which slot the pin is engaged, which also permits opening and closing of the box by a vertical movement of the lid.

8. Box according to claim 7, wherein the container comprises an outer collar and the lid comprises an inner wall and an outer wall, the pin being provided on the inner wall of the lid and the slot being provided in the collar of the container.

9. Box according to claim 7, wherein the slot in the collar of the container comprises two stop faces in order to limit opening of the lid.

10. Box according to claim 6, wherein the lid is equipped with an operating tappet which facilitates its articulation.

11. A set of boxes comprising a flexible sealing strip and a plurality of boxes according to claim 1, disposed one behind another on the strip, each box being fixed to the strip by its sealing region and external bottom wall, the strip acting as said protective concave cover for each box.

12. Set of boxes according to claim 11, wherein the plurality boxes are disposed on a single face of the strip.

13. Set of boxes according to claim 11, wherein the boxes are disposed alternately on either side of the strip.

* * * * *